United States Patent
Nilsson et al.

(10) Patent No.: US 9,452,149 B2
(45) Date of Patent: Sep. 27, 2016

(54) DIALYSIS COMPOSITION COMPRISING CITRATE, CALCIUM AND MAGNESIUM

(71) Applicant: GAMBRO LUNDIA AB, Lund (SE)

(72) Inventors: Anders Nilsson, Sodra Sandby (SE); Jan Sternby, Lund (SE); Anders Wieslander, Lund (SE)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 14/383,178

(22) PCT Filed: Mar. 5, 2013

(86) PCT No.: PCT/EP2013/054386
§ 371 (c)(1),
(2) Date: Sep. 5, 2014

(87) PCT Pub. No.: WO2013/131906
PCT Pub. Date: Sep. 12, 2013

(65) Prior Publication Data
US 2015/0024068 A1    Jan. 22, 2015

Related U.S. Application Data

(60) Provisional application No. 61/608,660, filed on Mar. 9, 2012.

(30) Foreign Application Priority Data

Mar. 8, 2012 (SE) ...................... 1250217

(51) Int. Cl.
*A61K 31/194* (2006.01)
*A61K 33/06* (2006.01)
*A61K 33/14* (2006.01)

(52) U.S. Cl.
CPC ............ *A61K 31/194* (2013.01); *A61K 33/06* (2013.01); *A61K 33/14* (2013.01)

(58) Field of Classification Search
CPC ........... A61K 2300/00; A61K 31/194; A61K 33/06; A61K 33/14
See application file for complete search history.

(56) References Cited

U.S. PATENT DOCUMENTS

| | | |
|---|---|---|
| 6,610,206 B1 | 8/2003 | Callan et al. |
| 2009/0306002 A1 | 12/2009 | Nakanishi et al. |

(Continued)

FOREIGN PATENT DOCUMENTS

| | | |
|---|---|---|
| EP | 1 731 183 | 12/2006 |
| EP | 1834652 | 9/2007 |

(Continued)

OTHER PUBLICATIONS

Ahmad et al., "Dialysate Made From Dry Chemicals Using Citric Acid Increases Dialysis Dose," American Journal of Kidney Diseases, vol. 35, No. 3 (March), 2000: pp. 493-499.
Gabutti et al., "Citrate- vs. acetate-based dialysate in bicarbonate haemodialysis: consequences on haemodynamics, coagulation, acid-base status, and electrolytes," BMC Nephrology 2009, 10:7.
Nilsson, "Citrate vs. Acetate in Bicarbonate-Based Dialysis Fluid—What Does it Mean Clinically?" Gambro Lundia AB, 2012.

(Continued)

*Primary Examiner* — Aradhana Sasan
(74) *Attorney, Agent, or Firm* — K&L Gates LLP

(57) ABSTRACT

Dialysis fluid compositions including 0.5 to 3 mM citrate, 1 to 5 mM total calcium, and 0 to 1.5 mM total magnesium. These dialysis fluid compositions include 0.10 to 0.2 mM more total calcium per 1 mM citrate within the dialysis fluid as compared to the calcium concentration ordinarily prescribed for a non-citrate containing dialysis fluid.

13 Claims, 2 Drawing Sheets

(56) References Cited

U.S. PATENT DOCUMENTS

2011/0172583 A1* 7/2011 Callan et al. ............... 604/5.04
2012/0291875 A1   11/2012 Shah et al.

FOREIGN PATENT DOCUMENTS

| EP | 2119438 | 11/2009 |
|----|---------|---------|
| EP | 2123270 | 11/2009 |
| JP | 2003104869 | 4/2003 |
| WO | 01/21233 | 3/2001 |
| WO | 2005002599 | 1/2005 |
| WO | 2010/055963 | 5/2010 |
| WO | 2010/112547 | 10/2010 |
| WO | 2010/112570 | 10/2010 |
| WO | 2011/161055 | 12/2011 |
| WO | 2011/161056 | 12/2011 |
| WO | 2012/175353 | 12/2012 |
| WO | 2012/175354 | 12/2012 |
| WO | 2013/004362 | 1/2013 |

OTHER PUBLICATIONS

Gambro Lundia AB's Response to Opposition filed in related European patent application No. 11729087.4 on Aug. 5, 2016.

Kipouros et al., "A Thermal Analysis of the Production of Anhydrous MgCl2," Journal of Light Metals, May 2001 (reference D4 cited in Response to Opposition filed in related European patent application No. 11729087.4 on Aug. 5, 2016).

Declaration of David Karlsson relating to film thickness, dated Jul. 29, 2016 (reference D5 cited in Response to Dpposition filed in related European patent application No. 11729087.4 on Aug. 5, 2016).

Annex A (curriculum vitae) of David Karlsson Declaration (annex to reference D5 cited in Response to Opposition filed in related European patent application No. 1172908T4 on Aug. 5, 2016).

Translation Declaration signed by Don Sanderson on Jul. 22, 2016 attesting to the translation of selected paragraphs 3f Jp 10-87478 (reference D2 cited by opponent Fresenius Medical Care), (reference D6 cited in Response to Dpposition filed in related European patent application No. 11729087.4 on Aug. 5, 2016).

Experimental annex providing stability data (reference D7 cited in Response to Opposition filed in related European patent application No. 11729087.4 on Aug. 5, 2016).

\* cited by examiner

DIALYSIS COMPOSITION COMPRISING CITRATE, CALCIUM AND MAGNESIUM

This application is a U.S. National Phase of International Application No. PCT/EP2013/054386 filed on 5 Mar. 2013, and claims priority to U.S. Provisional Application No. 61/608,660 filed on 9 Mar. 2012 and Swedish Patent Application No. 1250217-5 filed on 8 Mar. 2012, the entire contends to each of these applications is incorporated by reference.

TECHNICAL FIELD

The present invention concerns dialysis compositions, and more specifically dialysis compositions comprising citrate, calcium, and magnesium.

BACKGROUND

Dialysis is a well established treatment technique for patients having kidney malfunction. The dialysis treatment artificially replaces the functions of the kidney. There are two distinct types of dialysis, hemodialysis and peritoneal dialysis.

Hemodialysis involves withdrawing blood from the body and cleaning it in an extracorporeal blood circuit and then returning the cleansed blood to the body. The extracorporeal blood circuit includes a dialyzer which comprises a semipermeable membrane. The semipermeable membrane has a blood side and a dialysate side, and waste substances and excess fluid are removed from the blood passing on the blood side of the semipermeable membrane through the semipermeable membrane over to the dialysate side of the semipermeable membrane.

Hemodialysis may be performed in three different treatment modes, hemodialysis, hemofiltration, and hemodiafiltration. Common to all three treatment modes is that the patient is connected by a blood line to the dialysis machine, which continuously withdraws blood from the patient. The blood is then brought in contact with the blood side of the semipermeable membrane within the dialyzer in a flowing manner.

In hemodialysis, an aqueous solution called dialysis fluid is brought in contact with the opposite membrane surface, the dialysate side, in a flowing manner. Waste substances (toxins) and solutes are removed/controlled mainly by diffusion. Excess fluid is removed by applying transmembrane pressure over the semipermeable membrane. Solutes and nutrients may diffuse in the opposite direction from the dialysis fluid, through the semipermeable membrane and into the blood.

In hemofiltration, no dialysis fluid is brought in contact with the dialysate side of the semipermeable membrane. Instead only a transmembrane pressure is applied over the semipermeable membrane thereby removing fluid and waste substances, from the blood through the semipermeable membrane wall and into the dialysate side thereof (convective flow). Fluid and waste substances are then passed to drain. To replace some of the removed fluid, a correctly balanced electrolyte/buffer dialysis fluid (also named infusion fluid, replacement fluid, or substitution fluid) is infused into the extracorporeal blood circuit. This infusion may be done either pre the dialyzer (pre-infusion mode) or post the dialyzer (post-infusion mode) or both.

Hemodiafiltration is a combination of hemodialysis and hemofiltration, a treatment mode that combines transport of waste substances and excess fluids through the semipermeable wall by both diffusion and convection. Thus, here a dialysis fluid is brought in contact with the dialysate side of the semipermeable membrane in a continuously flowing manner, and a dialysis fluid (also named infusion fluid or replacement fluid) is used for infusion into the extracorporeal blood circuit in pre-infusion mode, post-infusion mode or both.

For many patients, hemodialysis is performed for 3-5 hours, three times per week. It is usually performed at a dialysis centre, although home dialysis is also possible.

When home dialysis is performed patients are free to perform dialysis more frequently and also in more gentle treatments with longer treatment times, i.e. 4-8 hours per treatment and 5-7 treatments per week. The dose and treatment times may be adjusted due to different demand of the patients.

In the case of patients suffering from acute renal insufficiency, a continuous treatment, throughout a major portion of the entire day for up to several weeks, a continuous renal replacement therapy (CRRT), or intermittent renal replacement therapy (IRRT) is the indicated treatment depending on the patients status. Also here the removal of waste substances and excess fluid from the patient is effected by any or a combination of the treatment modes hemodialysis, hemofiltration and hemodiafiltration.

In a peritoneal dialysis treatment a hypertonic dialysis fluid is infused into the peritoneal cavity of the patient. In this treatment solutes and water is exchanged in the capillary vessels of a patient's peritoneal membrane with said hypertonic dialysis fluid. The principle of this method is diffusion of solutes transferred according to the concentration gradient and water migration due to the osmotic differences over the peritoneal membrane.

The dialysis fluids used in all the above dialysis techniques contain mainly electrolytes like sodium, magnesium, calcium, potassium, an acid/base buffer system and optionally glucose or a glucose-like compound. All the components in dialysis fluids are selected to control the levels of electrolytes and the acid-base equilibrium within the blood and to remove waste materials from the blood.

Dialysis fluids are today prepared from different types of concentrates. These may be liquid concentrates of different degree of concentration, where the acid/-electrolyte part may be separated from the buffer part.

It may be provided as liquid concentrates divided between different compartments within a multi-compartment bag. These liquid concentrates are then mixed to prepare the dialysis fluid. This mixing may be performed by breaking a seal between the different compartments, but it may also be performed by having the different liquid concentrates being led from the different compartments to a fluid preparation unit for mixing therein into a dialysis fluid.

The concentrates may further be provided in highly concentrated volumes of 1-8 L in bags for bedside use, or in more diluted concentrated volumes of 5-20 L in canisters, which still are for bedside use, both for mixing within a fluid preparation unit into a dialysis fluid.

The concentrates may also be provided as dry concentrates for dilution into liquid concentrates and further mixing within a fluid preparation unit into a dialysis fluid.

Concentrates may also be prepared in central tanks in volumes of typically 300-1000 L.

As mentioned above, the dialysis fluid contains an acid for the acid/base buffer system. Historically the acid used within dialysis fluids has been acetic acid. However, in recent years citric acid has emerged as an alternative to acetic acid in dialysis fluids. While increased plasma levels of acetate may induce symptoms like general malaise, intradialytic hypotension and nausea, citrate is a natural source of energy for all cells and part of the acid-base regulation in the body. In addition, citrate is an anticoagulant and antioxidant with anti-inflammatory properties and may improve patient treatment tolerance.

However, clinical trials have shown that it is not just to replace acetic acid with citric acid. Citric acid has specific effects that need to be taken into consideration, namely its ability to form a complex with electrolytes within the dialysis fluid. This complex formation has to be compensated for when deciding on the concentrations of all the components within the dialysis fluid.

In M. Braide, et al., *Citrate supplementation of PD fluid: effects on net ultrafiltration and clearance of small solutes in single dwells*, Nephrol Dial Transplant (2009) 24:286-292, it is described that citrate containing solutions may affect the levels of calcium due to calcium chelating.

In WO01/21233 A1 a high citrate dialysate and uses thereof is disclosed. The application discloses a dialysate composition comprising citrate at a concentration ranging from 2.4 to 20 mEq/L (equals 0.8-6.67 mM citrate), calcium at a concentration ranging from 2.5 to 5 mEq/L (equals to 1.25-2.5 mM calcium), and magnesium at a concentration ranging from 1 to 2 mEq/L (equals 0.5-1.0 mM magnesium). One example of a composition is given in the application, a composition comprising 2.4 mEq/L (equals 0.8 mM) citric acid and 2.5 or 3 mEq/L (equals 1.25 or 1.5 mM) calcium, and 0.75 mEq/L (equals 0.375 mM) magnesium.

Thus, there is a need of guidance on how to combine different concentrations of citrate with calcium and magnesium.

SUMMARY OF THE INVENTION

One object of the present invention is to provide guidance on how to combine different concentrations of citrate and the electrolytes within a dialysis fluid without giving rise to unacceptable changes in electrolyte concentrations within the patient.

Another object of the present invention is to provide a dialysis composition with balanced concentrations of citrate and calcium.

Another object of the present invention is to provide a dialysis composition with balanced concentrations of citrate and magnesium.

Yet another object of the present invention is to provide a dialysis composition with balanced concentrations of citrate, calcium and magnesium.

The present invention concerns a dialysis composition comprising 0.5 to 3 mM citrate, 1 to 5 mM total calcium, and 0 to 1.5 mM total magnesium. According to the invention the dialysis composition comprises 0.10 to 0.2 mM more in total calcium per 1 mM citrate within the dialysis fluid, in comparison with ordinary prescribed calcium concentration.

In one embodiment of the invention the dialysis composition comprises 0.5 to 3 mM citrate, 1 to 5 mM total calcium, and 0.5 to 1.5 mM total magnesium. According to the invention the dialysis composition, comprises 0.10 to 0.2 mM more in total calcium per 1 mM citrate within the dialysis fluid, in comparison with ordinary prescribed calcium concentration.

In one embodiment the dialysis composition comprises 0.12 to 0.18 mM more in total calcium per 1 mM citrate within the dialysis fluid, in comparison with ordinary prescribed calcium concentration.

In another embodiment the dialysis composition comprises 0.15 mM more in total calcium per 1 mM citrate within the dialysis fluid, in comparison with ordinary prescribed calcium concentration.

In yet another embodiment the dialysis composition comprises 0.04-0.10 mM more total magnesium per 1 mM citrate within the dialysis fluid, in comparison with ordinary prescribed magnesium concentration.

In even another embodiment the dialysis composition comprises 0.06-0.08 mM more total magnesium per 1 mM citrate within the dialysis fluid, in comparison with ordinary prescribed magnesium concentration.

In even a further embodiment the dialysis composition according comprises 0.07 mM more total magnesium per 1 mM citrate within the dialysis fluid, in comparison with the ordinary prescribed magnesium concentration.

The present invention further concerns a dialysis composition comprising 0.5 to 3 mM citrate, 1 to 5 mM total calcium, and 0 to 1.5 mM total magnesium, wherein the dialysis composition comprises [cit] mM citrate and $[Ca]_{new}$ mM total calcium, wherein $$[Ca]_{new}=[Ca]_{norm}+(k_{Ca}\cdot[\text{cit}]).$$

$k_{Ca}$ is within range 0.10-0.2, range 0.12-0.18 or equals 0.15.

The present invention further concerns a dialysis composition comprising 0.5 to 3 mM citrate, 1 to 5 mM total calcium, and 0 to 1.5 mM total magnesium, wherein the dialysis composition comprises [cit] mM citrate and $[Ca]_{new}$ mM total calcium, wherein $$[Ca]_{new}=[Ca]_{norm}+(k_{Ca}\cdot[\text{cit}]),$$

and wherein $[Ca]_{norm}$ is within the range, 1 to 5 mM calcium, range 1 to 3 mM calcium.

$k_{Ca}$ is within range 0.10-0.2, range 0.12-0.18 or equals 0.15.

The present invention further concerns a dialysis composition comprising 0.5 to 3 mM citrate, 1 to 5 mM total calcium, and 0 to 1.5 mM total magnesium, wherein the dialysis composition comprises [cit] mM citrate and $[Ca]_{new}$ mM total calcium, wherein $$[Ca]_{new}=[Ca]_{norm}+(k_{Ca}\cdot[\text{cit}]),$$

and wherein $[Ca]_{norm}$ equals 1.00 mM, 1.25 mM, 1.5 mM, or 1.75 mM calcium.

$k_{Ca}$ is within range 0.10-0.2, range 0.12-0.18 or equals 0.15.

The present invention further concerns a dialysis composition comprising 0.5 to 3 mM citrate, 1 to 5 mM total calcium, and 0.5 to 1.5 mM total magnesium, wherein the dialysis composition comprises [cit] mM citrate and $[Ca]_{new}$ mM total calcium, wherein $$[Ca]_{new}=[Ca]_{norm}+(k_{Ca}\cdot[\text{cit}]).$$

$k_{Ca}$ is within range 0.10-0.2, range 0.12-0.18 or equals 0.15.

The present invention further concerns a dialysis composition comprising 0.5 to 3 mM citrate, 1 to 5 mM total calcium, and 0.5 to 1.5 mM total magnesium, wherein the dialysis composition comprises [cit] mM citrate and $[Ca]_{new}$ mM total calcium, wherein $$[Ca]_{new}=[Ca]_{norm}+(k_{Ca}\cdot[\text{cit}]).$$

and wherein

[Ca]$_{norm}$ is within the range, 1 to 5 mM calcium, range 1 to 3 mM calcium.

k$_{ca}$ is within range 0.10-0.2, range 0.12-0.18 or equals 0.15.

The present invention further concerns a dialysis composition comprising 0.5 to 3 mM citrate, 1 to 5 mM total calcium, and 0.5 to 1.5 mM total magnesium, wherein the dialysis composition comprises [cit] mM citrate and [Ca]$_{new}$ mM total calcium, wherein

[Ca]$_{new}$=[Ca]$_{norm}$+(k$_{Ca}$·[cit]).

and wherein

[Ca]$_{norm}$ equals 1.00 mM, 1.25 mM, 1.5 mM, or 1.75 mM calcium.

k$_{ca}$ is within range 0.10-0.2, range 0.12-0.18 or equals 0.15.

In one embodiment of this dialysis composition, the dialysis composition further comprises [Mg]$_{new}$ mM total magnesium, wherein

[Mg]$_{new}$=[Mg]$_{norm}$+(k$_{Mg}$·[cit]).

and wherein

[Mg]$_{norm}$ is within range 0 to 1.5 mM, and

K$_{Mg}$ is within range 0.04-0.10, range 0.06-0.08 or equals 0.07.

In one embodiment of this dialysis composition, the dialysis composition further comprises [Mg]$_{new}$ mM total magnesium, wherein

[Mg]$_{new}$=[Mg]$_{norm}$+(k$_{Mg}$·[cit]).

and wherein

[Mg]$_{norm}$ is within range 0.5 to 1.5 mM, and

K$_{Mg}$ is within range 0.04-0.10, range 0.06-0.08 or equals 0.07.

In one embodiment of this dialysis composition, the dialysis composition further comprises [Mg]$_{new}$ mM total magnesium, wherein

[Mg]$_{new}$=[Mg]$_{norm}$+(k$_{Mg}$·[cit]).

and wherein

[Mg]$_{norm}$ equals 0.50 mM, 0.60 mM, or 0.75 mM magnesium, and

K$_{mg}$ is within range 0.04-0.10, range 0.06-0.08 or equals 0.07.

Other embodiments of the present invention is evident from the description below.

All of the disclosed embodiments may not fulfill the disclosed objectives.

DEFINITIONS

Figure 1:
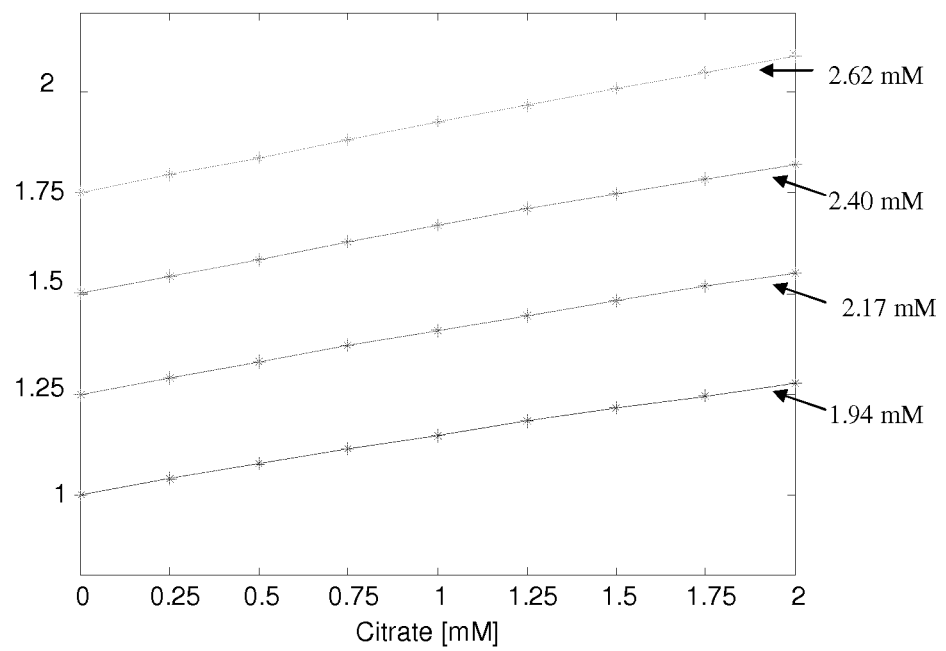
FIG. 1 shows the concentration of total calcium needed in the dialysis fluid as a function of the citrate concentration to keep the same total calcium concentration in the blood outlet, i.e. to get a constant transport of calcium irrespectively of the citrate level.

The term "dialysis composition" means the composition of dialysis fluids for hemodialysis, hemodiafiltration, hemofiltration, and peritoneal dialysis, fluids for dialysis within renal intensive care, fluids for substitution or infusion normally containing buffering substances.

The term "citrate" means that the component may be added as citric acid or any salt thereof, such as its sodium, magnesium, calcium or potassium salt thereof, i.e. citrate, to the dialysis composition. However, after mixing thereof with the remaining components including the buffer, citric acid is normally converted into citrate within the fluid.

The term "total citrate" refers to the total amount of citrate present in a fluid, thus representing the sum of citrate present as ionized citrate and complex bound citrate.

The term "total calcium concentration" refers to the total amount of calcium present in a fluid, thus representing the sum of calcium present as ionized calcium, and complex bound calcium including protein bound calcium (mostly albumin bound).

The term "total magnesium concentration" refers to the total amount of magnesium present in a fluid, thus representing the sum of magnesium present as ionized magnesium, and complex bound magnesium including protein bound magnesium (mostly albumin bound).

The term "ordinary prescribed calcium concentration" means the calcium concentration that is prescribed to the patient when a non-citrate containing dialysis fluid is used. This concentration is normally 1.00 mM, 1.25 mM, 1.5 mM, or 1.75 mM, dependent on calcium concentration and calcium mass transport for that specific patient. This is individual and depends on food intake, different type of medication, such as calcium containing phosphate binders and Vitamin D and so forth, since last dialysis session and the imbalance already summoned during earlier dialysis and food intake.

The term "ordinary prescribed magnesium concentration" means the magnesium concentration that is prescribed to patient when a non-citrate containing dialysis fluid is used. This concentration is normally 0.5 mM, 0.6 mM or 0.75 mM, dependent on magnesium concentration and magnesium mass transport for that specific patient.

The term [cit] means the total citrate concentration within the dialysis composition as defined above.

The term [Ca]$_{new}$ means the total calcium concentration to be used in the dialysis composition according to the invention.

The term [Ca]$_{norm}$ means the ordinary prescribed calcium concentration, see above for further definition.

The term k$_{ca}$ means the amount (mM) calcium that needs to be added to the citrate containing dialysis composition per 1 mM citrate in addition to the ordinary prescribed calcium concentration, [Ca]$_{norm}$.

The term [Mg]$_{new}$ means the total magnesium concentration to be used in the dialysis composition according to the invention.

The term [Mg]$_{norm}$ means the ordinary prescribed magnesium concentration, see above for further definition.

The term k$_{Mg}$ means the amount (mM) magnesium that needs to be added to the citrate containing dialysis composition per 1 mM citrate in addition to the ordinary prescribed magnesium concentration, [Mg]$_{norm}$.

DETAILED DESCRIPTION OF THE INVENTION

As stated above, when using citrate within dialysis compositions, one specific effect has to be taken into account, namely its ability to form a complex with, in particular, divalent electrolytes like calcium and magnesium.

When some plasma calcium, i.e. the calcium ionized within the patient's blood, is complex bound to citrate, the level of free ionized calcium will decrease, and some calcium will then be released from albumin. The fraction of total calcium that is bound to albumin will then decrease. Both the free ionized calcium and the calcium citrate complexes are able to pass the dialyzer membrane, and there will thus be an increased force driving calcium from the blood to the dialysate. In order to maintain the same calcium balance in the patient with citrate as with acetate in the dialysis composition it is necessary to increase the calcium level in the dialysis fluid if the citrate level is increased.

The transport rate of various substances across the semipermeable membrane in the dialyzer is quantified by a clearance value, which is defined as the transport rate divided by the blood inlet concentration. For solutes that are present also in the dialysis fluid the term dialysance is used instead of clearance, and the driving force for the transport is the concentration difference. For small, uncharged, water soluble compounds like urea or creatinine it has been known since long how to theoretically calculate clearance/dialysance in hemodialysis from the blood and dialysis fluid flow rates and dialyzer characteristics, the so called mass transfer area coefficient koA[1]. These formulas were later extended to hemodiafiltration, where significant ultrafiltration takes place[2-4]. Based on a theory[5] of the additional effects of electrical forces on charged particles in membrane transport new formulas have been derived for clearance/dialysance of charged substances when the electrical potential across the membrane (membrane potential) is known. If required such a potential arises to maintain electroneutrality[6]. In order to quantify the membrane potential we use the formulas to calculate all transports of charged substances with a guessed potential. The membrane potential is then adjusted in an iterative manner until the total transports of positive and negative charges across the membrane are equal. This illustrates that all charged substances, both complex bound substances and ions, act together. It is not possible to calculate the isolated transport for just one ion.

It is also necessary to handle the complex binding. The transport of each complex across the membrane is governed by the forces discussed above, just as for other substances. But when the complex leaves one side of the membrane its concentration will decrease, and this will affect the equilibrium between the complex and its components. The corresponding is true on the other side of the membrane when the concentration of the complex increases. These changes in the equilibriums will also affect the transport across the membrane, and it is necessary to include the equilibrium equations in the calculation of the transports.

The mass transfer area coefficients of the various substances are also needed in the calculations. The value for urea is obtained from the clearance values given by the dialyzer manufacturer. The value for potassium is derived to 70% of the urea value by comparing clearances[7] for urea and potassium at blood flow of 200 ml/min and dialysis fluid flow of 500 ml/min. For a large number of other substances data may be found in literature relating their mobility to the mobility of potassium[8]. The mass transfer area coefficients are proportional to the mobility, and the mass transfer area coefficient for other substances may therefore be derived from that of potassium. Values for substances that could not be found in literature may be found by interpolation from substances with similar molecular weight.

One important substance in blood is albumin, which binds several other substances like sodium, calcium, magnesium and hydrogen ions. Each albumin molecule has the ability to bind a large number of these ions (pH dependent) with different equilibrium constants[9]. Both calcium and magnesium ions may bind also to bicarbonate and citrate. These equilibrium constants were also found in literature[10].

To calculate the complex transport across a semipermeable membrane in a dialyzer, the dialyzer is divided into a number (5-20) of subdialyzers along its entire length. In each subdialyzer the transport of each substance and each complex are considered separately, but using a membrane potential to maintain electroneutrality. With the given inlet concentrations for each substance the outlet concentrations are calculated from the transports. The total concentrations of each basic compound are then calculated by summing their free concentrations and the concentrations of all the complexes where they appear. These total concentrations are then used to calculate a new distribution between free concentrations and the relevant complexes according to the respective equilibrium constants. These recalculated concentrations are then used as input to the next subdialyzer. About 30 iterations along the whole dialyzer are needed to reach a steady state situation.

When citrate is added to the dialysis fluid and transfers into the blood stream in the dialyzer it will bind to calcium and this will cause more calcium to be released from albumin as explained above. The level of ionized calcium is therefore deranged in the blood in the dialyzer. But when this blood is returned to the patient and meets the large blood volume there, a new equilibrium will be established. In contrast to the dialyzer blood, the citrate level in the patient will still be low, and very little calcium will be bound to citrate. The complexes in the blood from the dialyzer will be diluted in the large blood volume in the patient, and this will change the equilibrium so that most of the calcium is released. Since the level of ionized calcium thus changes quite a lot as soon as the blood is returned to the patient it is not possible to base the calcium level in the dialysis fluid on the concentration of ionized calcium.

On the contrary, the total calcium level will not change if the citrate level changes. Our assumption is therefore that the total concentration of calcium (i.e. the sum of free calcium, complex bound and albumin bound calcium) in the blood returned to the patient should be independent of the amount of citrate in the dialysis fluid. What this means is evaluated by simulating treatments with varying levels of citrate in the dialysis fluid.

The calculations were first performed with blood inlet total calcium concentration of 2.4 mM. The blood flow rate was 300 ml/min, the dialysis fluid flow rate 500 ml/min, koA of the dialyzer (for urea) was 1000 ml/min. The dialysis fluid inlet calcium values without citrate were chosen to 1, 1.25, 1.5 and 1.75 mM which gave blood outlet values for total calcium of 1.94, 2.17, 2.40 and 2.62 mM, respectively. Next the dialysis fluid inlet calcium values necessary to maintain the same blood outlet total calcium values (thus maintaining the same calcium transport across the membrane) were determined for citrate levels of 0-2 mM in steps of 0.25 mM.

In FIG. 1 the concentration of total calcium needed in the dialysis fluid is shown as a function of the citrate concentration to keep the same total calcium concentration in the blood outlet, i.e. to get a constant transport of calcium irrespectively of the citrate level. Results are shown for four different levels of calcium transfer between blood and dialysis fluid, all with a total calcium of 2.4 mM at the blood inlet.

It turns out that the need for calcium in the dialysis fluid increases almost linearly with the citrate level, and the slopes are almost equal for the different initial calcium levels, about 0.15 mM calcium for each mM of citrate. These results are shown in FIG. 1, displaying the required total calcium levels in the dialysis fluid as functions of the citrate level for the four different calcium levels at zero citrate. Noted in the end of each line are the resulting total calcium levels at the blood outlet.

These calculations were then repeated for blood flow rates between 200-400 ml/min, for a dialysis fluid flow rate of 800 ml/min and for koA (urea)=700 ml/min. The total calcium levels in the blood outlet became different in the different cases, but interestingly enough, in all cases the requirement for the calcium level in the dialysis fluid still increases with about 0.15 mM per mM of citrate.

Thus, when citrate is added to the dialysis fluid, the calcium level needs to be increased by about 0.10 to 0.2 mM for each 1 mM of citrate, or 0.12 to 0.18 mM for each 1 mM citrate, or 0.15 mM for each mM of citrate.

The citrate added to the dialysis fluid and transferred into the blood stream in the dialyzer will also bind to magnesium and the same situation as with calcium will apply with magnesium.

The calculations with magnesium were performed in a similar manner, and were first performed with blood inlet total magnesium concentration of 0.96 mM. The blood flow rate was 300 ml/min, the dialysis fluid flow rate 500 ml/min, koA of the dialyzer (for urea) was 1000 ml/min. The dialysis fluid inlet magnesium values without citrate were chosen to 0.5, 0.6, and 0.75 mM which gave blood outlet values for total magnesium of 0.87, 0.95, and 1.07 mM, respectively. Next the dialysis fluid inlet magnesium values necessary to maintain the same blood outlet total magnesium values (thus maintaining the same magnesium transport across the membrane) were determined for citrate levels of 0-2 mM in steps of 0.25 mM.

Figure 2:
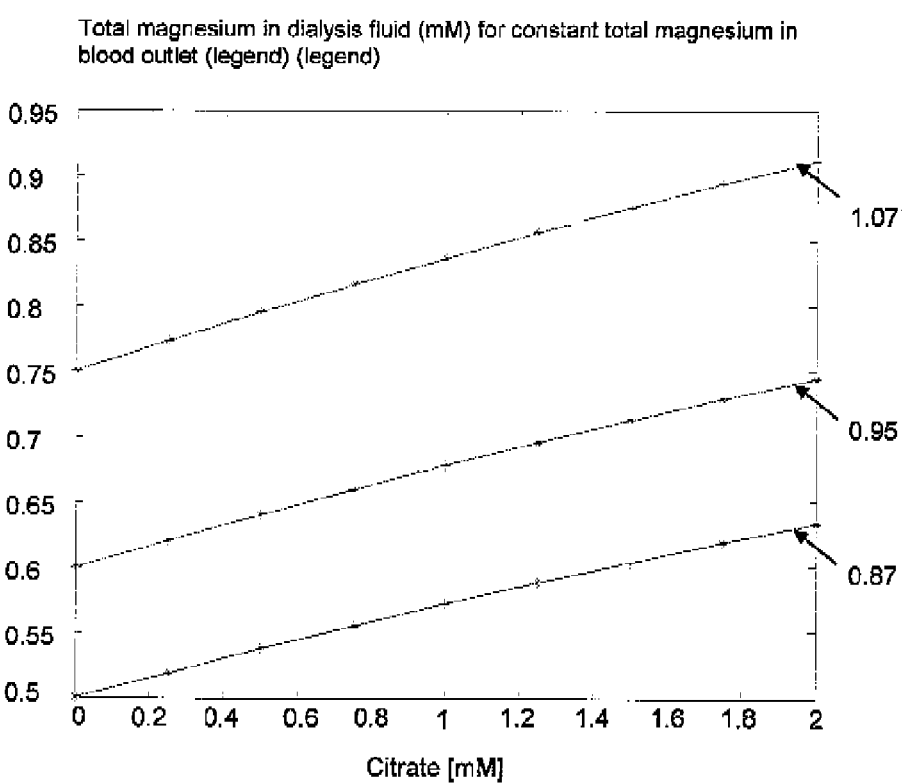
FIG. 2 shows the concentration of total magnesium needed in the dialysis fluid as a function of the citrate concentration to keep the same total magnesium concentration in the blood outlet, i.e. to get a constant transport of magnesium irrespectively of the citrate level.

In FIG. 2 the concentration of total magnesium needed in the dialysis fluid is shown as a function of the citrate concentration to keep the same total magnesium concentration in the blood outlet, i.e. to get a constant transport of magnesium irrespectively of the citrate level. Results are shown for three different levels of magnesium transfer between blood and dialysis fluid, all with a total magnesium of 0.96 mM at the blood inlet.

It turns out that the need for magnesium in the dialysis fluid also increases almost linearly with the citrate level, and the slopes are almost equal for the different initial magnesium levels, about 0.07 mM magnesium for each mM of citrate. These results are shown in FIG. 2, displaying the required total magnesium levels in the dialysis fluid as functions of the citrate level for the three different magnesium levels at zero citrate. Noted in the end of each line are the resulting total magnesium levels at the blood outlet.

Thus, when citrate is added to the dialysis fluid the magnesium level needs to be increased by about 0.04 to 0.10 mM for each 1 mM of citrate, or 0.06 to 0.08 mM for each 1 mM citrate, or 0.07 mM for each 1 mM of citrate.

EXAMPLES

By way of example, and not limitation, the following examples identify a variety of dialysis compositions pursuant to embodiments of the present invention.

Example 1

In table 1a electrolyte concentrations within different acetate containing dialysis fluid are given, one row for each dialysis fluid (Examples 1a:1-1a:25).

In table 1b electrolyte concentrations within corresponding citrate containing dialysis fluids are given, wherein the same row shows the corresponding electrolyte concentration needed to keep the patient's calcium mass balance unchanged in comparison when using a dialysis fluid not containing any citrate (Examples 1b:1-1b:25).

However, all these dialysis fluids, both acetate and citrate containing dialysis fluids, further contain about 130-150 mM sodium, 135-145 mM sodium or 140 mM sodium, and 20-40 mM bicarbonate, 25-35 mM bicarbonate or 34 mM bicarbonate, and chloride determined by electroneutrality.

TABLE 1a

Electrolyte concentrations in acetate dialysis fluids

| Example: | $K^+$ mM | $Ca^{2+}$ mM | $Mg^{2+}$ mM | Acetate mM | Gluc. g/l |
|---|---|---|---|---|---|
| 1a:1  | 1   | 1.00 | 0.5 | 3 | 1 |
| 1a:2  | 1   | 1.25 | 0.5 | 3 | 1 |
| 1a:3  | 1   | 1.50 | 0.5 | 3 | 1 |
| 1a:4  | 1   | 1.75 | 0.5 | 3 | 1 |
| 1a:5  | 2   | 1.00 | 0.5 | 3 | 1 |
| 1a:6  | 2   | 1.25 | 0.5 | 3 | 1 |
| 1a:7  | 2   | 1.50 | 0.5 | 3 | 1 |
| 1a:8  | 2.5 | 1.25 | 0.5 | 3 | 1 |
| 1a:9  | 2.5 | 1.50 | 0.5 | 3 | 1 |
| 1a:10 | 2   | 1.75 | 0.5 | 3 | 1 |
| 1a:11 | 3   | 1.25 | 0.5 | 3 | 1 |
| 1a:12 | 3   | 1.50 | 0.5 | 3 | 1 |
| 1a:13 | 3   | 1.75 | 0.5 | 3 | 1 |
| 1a:14 | 4   | 1.25 | 0.5 | 3 | 1 |
| 1a:15 | 4   | 1.50 | 0.5 | 3 | 1 |
| 1a:16 | 4   | 1.75 | 0.5 | 3 | 1 |
| 1a:17 | 0   | 1.50 | 0.5 | 3 | 0 |
| 1a:18 | 1   | 1.25 | 0.5 | 3 | 0 |
| 1a:19 | 1   | 1.50 | 0.5 | 3 | 0 |
| 1a:20 | 2   | 1.25 | 0.5 | 3 | 0 |
| 1a:21 | 2   | 1.50 | 0.5 | 3 | 0 |
| 1a:22 | 2   | 1.75 | 0.5 | 3 | 0 |
| 1a:23 | 3   | 1.25 | 0.5 | 3 | 0 |
| 1a:24 | 3   | 1.50 | 0.5 | 3 | 0 |
| 1a:25 | 3   | 1.75 | 0.5 | 3 | 0 |

TABLE 1b

Electrolyte concentrations in corresp. citrate dialysis fluids

| Example: | $K^+$ mM | $Ca^{2+}$ mM | $Mg^{2+}$ mM | Citrate mM | Gluc. g/l |
|---|---|---|---|---|---|
| 1b:1  | 1   | 1.20 | 0.5 | 1 | 1 |
| 1b:2  | 1   | 1.45 | 0.5 | 1 | 1 |
| 1b:3  | 1   | 1.60 | 0.5 | 1 | 1 |
| 1b:4  | 1   | 1.87 | 0.5 | 1 | 1 |
| 1b:5  | 2   | 1.15 | 0.5 | 1 | 1 |
| 1b:6  | 2   | 1.40 | 0.5 | 1 | 1 |
| 1b:7  | 2   | 1.65 | 0.5 | 1 | 1 |
| 1b:8  | 2.5 | 1.37 | 0.5 | 1 | 1 |
| 1b:9  | 2.5 | 1.60 | 0.5 | 1 | 1 |
| 1b:10 | 2   | 1.90 | 0.5 | 1 | 1 |
| 1b:11 | 3   | 1.45 | 0.5 | 1 | 1 |
| 1b:12 | 3   | 1.60 | 0.5 | 1 | 1 |
| 1b:13 | 3   | 1.87 | 0.5 | 1 | 1 |
| 1b:14 | 4   | 1.40 | 0.5 | 1 | 1 |
| 1b:15 | 4   | 1.65 | 0.5 | 1 | 1 |
| 1b:16 | 4   | 1.85 | 0.5 | 1 | 1 |
| 1b:17 | 1   | 1.70 | 0.5 | 1 | 0 |
| 1b:18 | 1   | 1.43 | 0.5 | 1 | 0 |
| 1b:19 | 1   | 1.65 | 0.5 | 1 | 0 |
| 1b:20 | 2   | 1.45 | 0.5 | 1 | 0 |
| 1b:21 | 2   | 1.62 | 0.5 | 1 | 0 |
| 1b:22 | 2   | 1.85 | 0.5 | 1 | 0 |
| 1b:23 | 3   | 1.43 | 0.5 | 1 | 0 |

TABLE 1b-continued

Electrolyte concentrations in corresp. citrate dialysis fluids

| Example: | $K^+$ mM | $Ca^{2+}$ mM | $Mg^{2+}$ mM | Citrate mM | Gluc. g/l |
|---|---|---|---|---|---|
| 1b:24 | 3 | 1.62 | 0.5 | 1 | 0 |
| 1b:25 | 3 | 1.85 | 0.5 | 1 | 0 |

Example 2

In table 2a electrolyte concentrations within different acetate containing dialysis fluids are given, one row for each dialysis fluid (Examples 2a:1-2a:25).

In table 2b electrolyte concentrations within corresponding citrate containing dialysis fluids are given, wherein the same row shows the corresponding electrolyte concentration needed to keep the patient's calcium and magnesium mass balance unchanged in comparison when using a dialysis fluid not containing any citrate (Examples 2b:1-2b:25).

Again, as indicated above, both acetate containing and citrate containing fluids further contain sodium, bicarbonate and chloride as indicated above.

TABLE 2a

Electrolyte concentrations in acetate dialysis fluids

| Example: | $K^+$ mM | $Ca^{2+}$ mM | $Mg^{2+}$ mM | Acetat mM | Gluc. g/l |
|---|---|---|---|---|---|
| 2a:1 | 1 | 1.00 | 0.5 | 3 | 1 |
| 2a:2 | 1 | 1.25 | 0.5 | 3 | 1 |
| 2a:3 | 1 | 1.50 | 0.5 | 3 | 1 |
| 2a:4 | 1 | 1.75 | 0.5 | 3 | 1 |
| 2a:5 | 2 | 1.00 | 0.5 | 3 | 1 |
| 2a:6 | 2 | 1.25 | 0.5 | 3 | 1 |
| 2a:7 | 2 | 1.50 | 0.5 | 3 | 1 |
| 2a:8 | 2.5 | 1.25 | 0.5 | 3 | 1 |
| 2a:9 | 2.5 | 1.50 | 0.5 | 3 | 1 |
| 2a:10 | 2 | 1.75 | 0.5 | 3 | 1 |
| 2a:11 | 3 | 1.25 | 0.5 | 3 | 1 |
| 2a:12 | 3 | 1.50 | 0.5 | 3 | 1 |
| 2a:13 | 3 | 1.75 | 0.5 | 3 | 1 |
| 2a:14 | 4 | 1.25 | 0.5 | 3 | 1 |
| 2a:15 | 4 | 1.50 | 0.5 | 3 | 1 |
| 2a:16 | 4 | 1.75 | 0.5 | 3 | 1 |
| 2a:17 | 0 | 1.50 | 0.5 | 3 | 0 |
| 2a:18 | 1 | 1.25 | 0.5 | 3 | 0 |
| 2a:19 | 1 | 1.50 | 0.5 | 3 | 0 |
| 2a:20 | 2 | 1.25 | 0.5 | 3 | 0 |
| 2a:21 | 2 | 1.50 | 0.5 | 3 | 0 |
| 2a:22 | 2 | 1.75 | 0.5 | 3 | 0 |
| 2a:23 | 3 | 1.25 | 0.5 | 3 | 0 |
| 2a:24 | 3 | 1.50 | 0.5 | 3 | 0 |
| 2a:25 | 3 | 1.75 | 0.5 | 3 | 0 |

TABLE 2b

Electrolyte concentrations in corresp. citrate dialysis fluids

| Example: | $K^+$ mM | $Ca^{2+}$ mM | $Mg^{2+}$ mM | Citrate mM | Gluc. g/l |
|---|---|---|---|---|---|
| 2b:1 | 1 | 1.20 | 0.57 | 1 | 1 |
| 2b:2 | 1 | 1.45 | 0.56 | 1 | 1 |
| 2b:3 | 1 | 1.60 | 0.54 | 1 | 1 |
| 2b:4 | 1 | 1.87 | 0.54 | 1 | 1 |
| 2b:5 | 2 | 1.15 | 0.60 | 1 | 1 |
| 2b:6 | 2 | 1.40 | 0.58 | 1 | 1 |
| 2b:7 | 2 | 1.65 | 0.57 | 1 | 1 |
| 2b:8 | 2.5 | 1.37 | 0.58 | 1 | 1 |
| 2b:9 | 2.5 | 1.60 | 0.58 | 1 | 1 |
| 2b:10 | 2 | 1.90 | 0.56 | 1 | 1 |
| 2b:11 | 3 | 1.45 | 0.54 | 1 | 1 |
| 2b:12 | 3 | 1.60 | 0.58 | 1 | 1 |
| 2b:13 | 3 | 1.87 | 0.57 | 1 | 1 |
| 2b:14 | 4 | 1.40 | 0.57 | 1 | 1 |
| 2b:15 | 4 | 1.65 | 0.58 | 1 | 1 |
| 2b:16 | 4 | 1.85 | 0.60 | 1 | 1 |
| 2b:17 | 1 | 1.70 | 0.54 | 1 | 0 |
| 2b:18 | 1 | 1.43 | 0.54 | 1 | 0 |
| 2b:19 | 1 | 1.65 | 0.57 | 1 | 0 |
| 2b:20 | 2 | 1.45 | 0.54 | 1 | 0 |
| 2b:21 | 2 | 1.62 | 0.58 | 1 | 0 |
| 2b:22 | 2 | 1.85 | 0.60 | 1 | 0 |
| 2b:23 | 3 | 1.43 | 0.54 | 1 | 0 |
| 2b:24 | 3 | 1.62 | 0.54 | 1 | 0 |
| 2b:25 | 3 | 1.85 | 0.58 | 1 | 0 |

Example 3

In table 3 electrolyte concentrations within different citrate containing dialysis fluids are given, wherein the column $[Ca]_{norm}$ shows ordinary prescribed calcium concentrations, while the column $[Ca]_{new}$ shows the total calcium concentration to be used in the citrate containing dialysis fluid.

The dialysis fluids according to Examples 3:1 to 3:24 further contain about 130-150 mM sodium, 135-145 mM sodium or 140 mM sodium, and 20-40 mM bicarbonate, 25-35 mM bicarbonate or 34 mM bicarbonate, 0-4 mM potassium, 0-2 g/L glucose and chloride determined by electroneutrality.

TABLE 3

| Example: | $[Ca]_{norm}$ mmol/L (mM) | Citrate mmol/L (mM) | $[Ca]_{new}$ mmol/L (mM) |
|---|---|---|---|
| 3:1 | 1.0 | 0.5 | 1.07 |
| 3:2 | 1.25 | 0.5 | 1.32 |
| 3:3 | 1.5 | 0.5 | 1.57 |
| 3:4 | 1.75 | 0.5 | 1.82 |
| 3:5 | 1.0 | 0.8 | 1.12 |
| 3:6 | 1.25 | 0.8 | 1.37 |
| 3:7 | 1.5 | 0.8 | 1.62 |
| 3:8 | 1.75 | 0.8 | 1.87 |
| 3:9 | 1.0 | 1.5 | 1.22 |
| 3:10 | 1.25 | 1.5 | 1.47 |
| 3:11 | 1.5 | 1.5 | 1.72 |
| 3:12 | 1.75 | 1.5 | 1.97 |
| 3:13 | 1.0 | 2.0 | 1.3 |
| 3:14 | 1.25 | 2.0 | 1.55 |
| 3:15 | 1.5 | 2.0 | 1.8 |
| 3:16 | 1.75 | 2.0 | 2.05 |
| 3:17 | 1.0 | 2.5 | 1.37 |
| 3:18 | 1.25 | 2.5 | 1.62 |
| 3:19 | 1.5 | 2.5 | 1.87 |
| 3:20 | 1.75 | 2.5 | 2.12 |
| 3:21 | 1.0 | 3.0 | 1.45 |
| 3:22 | 1.25 | 3.0 | 1.7 |
| 3:23 | 1.5 | 3.0 | 1.95 |
| 3:24 | 1.75 | 3.0 | 2.2 |

Example 4

In table 4 electrolyte concentrations within different citrate containing dialysis fluids are given, wherein the column $[Ca]_{norm}$ shows ordinary prescribed calcium concentrations and the column $[Mg]_{norm}$ shows ordinary prescribed magnesium concentration, while the column $[Ca]_{new}$ shows the total calcium concentration to be used in the citrate containing dialysis fluid and the column $[Mg]_{new}$ shows the total magnesium concentration to be used in the citrate containing dialysis fluid.

The dialysis fluids according to Examples 4:1 to 4:36 further contain about 130-150 mM sodium, 135-145 mM sodium or 140 mM sodium, and 20-40 mM bicarbonate, 25-35 mM bicarbonate or 34 mM bicarbonate, 0-4 mM potassium, 0-2 g/L glucose and chloride determined by electroneutrality.

TABLE 4

| Example: | $[Ca]_{norm}$ mmol/L (mM) | $[Mg]_{norm}$ mmol/L (mM) | Citrate mmol/L (mM) | $[Ca]_{new}$ mmol/L (mM) | $[Mg]_{new}$ mmol/L (mM) |
|---|---|---|---|---|---|
| 4:1 | 1.0 | 0.75 | 0.5 | 1.07 | 0.78 |
| 4:2 | 1.25 | 0.60 | 0.5 | 1.32 | 0.63 |
| 4:3 | 1.5 | 0.50 | 0.5 | 1.57 | 0.53 |
| 4:4 | 1.75 | 0.75 | 0.5 | 1.82 | 0.78 |
| 4:5 | 1.0 | 0.50 | 0.8 | 1.12 | 0.56 |
| 4:6 | 1.25 | 0.60 | 0.8 | 1.37 | 0.66 |
| 4:7 | 1.5 | 0.75 | 0.8 | 1.62 | 0.81 |
| 4:8 | 1.75 | 0.75 | 0.8 | 1.87 | 0.81 |
| 4:9 | 1.0 | 0.50 | 1.25 | 1.19 | 0.59 |
| 4:10 | 1.25 | 0.60 | 1.25 | 1.44 | 0.69 |
| 4:11 | 1.5 | 0.75 | 1.25 | 1.69 | 0.84 |
| 4:12 | 1.75 | 0.75 | 1.25 | 1.94 | 0.84 |
| 4:13 | 1.0 | 0.75 | 1.5 | 1.22 | 0.85 |
| 4:14 | 1.25 | 0.60 | 1.5 | 1.47 | 0.70 |
| 4:15 | 1.5 | 0.50 | 1.5 | 1.72 | 0.60 |
| 4:16 | 1.75 | 0.75 | 1.5 | 1.97 | 0.85 |
| 4:17 | 1.0 | 0.75 | 1.75 | 1.26 | 0.87 |
| 4:18 | 1.25 | 0.60 | 1.75 | 1.51 | 0.72 |
| 4:19 | 1.5 | 0.50 | 1.75 | 1.76 | 0.62 |
| 4:20 | 1.75 | 0.75 | 1.75 | 1.91 | 0.87 |
| 4:21 | 1.0 | 0.50 | 2.0 | 1.3 | 0.64 |
| 4:22 | 1.25 | 0.60 | 2.0 | 1.55 | 0.74 |
| 4:23 | 1.5 | 0.75 | 2.0 | 1.8 | 0.89 |
| 4:24 | 1.75 | 0.75 | 2.0 | 2.05 | 0.89 |
| 4:25 | 1.0 | 0.60 | 2.5 | 1.37 | 0.77 |
| 4:26 | 1.25 | 0.50 | 2.5 | 1.62 | 0.67 |
| 4:27 | 1.5 | 0.75 | 2.5 | 1.87 | 0.92 |
| 4:28 | 1.75 | 0.50 | 2.5 | 2.12 | 0.67 |
| 4:29 | 1.0 | 0.50 | 2.25 | 1.34 | 0.66 |
| 4:30 | 1.25 | 0.60 | 2.25 | 1.59 | 0.76 |
| 4:31 | 1.5 | 0.75 | 2.25 | 1.84 | 0.91 |
| 4:32 | 1.75 | 0.75 | 2.25 | 2.09 | 0.91 |
| 4:33 | 1.0 | 0.75 | 3.0 | 1.45 | 0.96 |
| 4:34 | 1.25 | 0.60 | 3.0 | 1.7 | 0.81 |
| 4:35 | 1.5 | 0.50 | 3.0 | 1.95 | 0.71 |
| 4:36 | 1.75 | 0.50 | 3.0 | 2.2 | 0.71 |

When increasing the amount of total citrate within the dialysis fluid, the amount of bicarbonate has to be adjusted towards the lower end if the ranges given above.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

REFERENCES

[1] Michels A: Operating parameters and performance criteria for hemodialyzers and other membrane-separation devices. Trans of the ASAIO 12, pp 387-392, 1966

[2] van Geelen J A, Carpay W, Dekkers W et al: Simultaneous hemodialysis and hemofiltration: A simple, safe and effective treatment of uremic patients. Proc ISAO, pp 119-122, 1979

[3] Waniewski J, Werynski A, Ahrenholz P et al: Theoretical Basis and Experimental Verification of the Impact of Ultrafiltration on Dialyzer Clearance. Artif Organs 15, pp 70-77, 1991

[4] Sternby J, Jönsson S, Ledebo I: Hemodiafiltration: Technical Aspects. In (Shaldon S, Koch K M, eds): Polyamide—The Evolution of a Synthetic Membrane for Renal Therapy. Contrib to Nephrology (Karger) 96, pp 86-98, 1992

[5] Lightfoot E N: Transport Phenomena in Living Systems. Wiley, New York, 1978

[6] Moore W J: Physical Chemistry, 5th edition. Longman, London, 1972

[7] Scharfetter H: Individually identifiable model for process optimization in clinical dialysis. Ph D Thesis at Graz University of Technology, Graz, June 1995

[8] Barry P H: Ionic Mobility Tables. http://web.med.unsw.edu.au/phbsoft/mobility_listings.htm, 2009

[9] van Leeuwen A M: Net cation equivalency (base binding power) of the plasma proteins. Acta Med Scand 176, Suppl 422, 1964

[10] Walser M: Ion association. VI. Interactions between calcium, magnesium, inorganic phosphate, citrate and protein in normal human plasma. J Clin Invest 40, pp 723-730, 1961

The invention claimed is:

1. A dialysis composition comprising 0.5 to 3 mM citrate, 1 to 5 mM total calcium, and 0 to 1.5 mM total magnesium, wherein the dialysis composition comprises [cit] mM citrate and $[Ca]_{new}$ mM total calcium, wherein $$[Ca]_{new}=[Ca]_{norm}+(k_{Ca}\cdot[cit]),$$

and wherein $k_{ca}$ is within range of 0.10 to 0.2.

2. The dialysis composition according to claim 1, wherein $[Ca]_{norm}$ is within the range of 1 to 5 mM and $k_{ca}$ is within range of 0.10 to 0.2.

3. The dialysis composition according to claim 1, wherein $[Ca]_{norm}$ equals one of 1.00 mM, 1.25 mM, 1.5 mM, and 1.75 mM calcium, and $k_{ca}$ is within range of 0.10 to 0.2.

4. The dialysis composition according to claim 1, wherein $[Ca]_{norm}$ equals at least one of 1.25 mM calcium and 1.5 mM calcium, and $k_{ca}$ is within range of 0.12 to 0.18.

5. The dialysis composition according to claim 1, wherein the dialysis composition further comprises $[Mg]_{new}$ mM total magnesium, wherein $$[Mg]_{new}=[Mg]_{norm}+(k_{mg}\cdot[cit]), \text{ and}$$

$k_{Mg}$ is within range of 0.04 to 0.10.

6. The dialysis composition according to claim 1, wherein $[Mg]_{norm}$ is in range of 0 to 1.5 mM, and $k_{Mg}$ is within range of 0.04 to 0.10.

7. The dialysis composition according to claim 1, wherein $[Mg]_{norm}$ is in range of 0.5 to 1.5 mM, and $k_{Mg}$ is within range of 0.04 to 0.10.

8. The dialysis composition according to claim 1, wherein $[Mg]_{norm}$ equals at least one of 0.50 mM, 0.60 and 0.75 mM magnesium, and $k_{Mg}$ is within range of 0.04 to 0.10.

9. A method to form a dialysis composition comprising: determining for a patient a prescribed calcium concentration for a dialysis fluid to be administered to the patient, wherein the determination is made based on a non-citrate containing calcium dialysis fluid;

introducing 0.5 to 3 mM citrate to the dialysis fluid, introducing 1 to 5 mM total calcium to the dialysis fluid, wherein the total calcium results in a calcium concentration 0.1 to 0.2 mM per 1 mM citrate greater than the prescribed calcium concentration; and introducing 0 to 1.5 mM total magnesium to the dialysis fluid.

10. The method of claim 9 wherein the determination of the prescribed calcium concentration determines the prescribed calcium concentration to be one of 1.00 mM, 1.25 mM, 1.50 mM, and 1.75 mM.

11. The method of claim 9 wherein the determination of the prescribed calcium concentration is based on at least one of calcium concentration and calcium mass transport for the patient.

12. The method of claim 9 further comprising:

determining a prescribed concentration of total magnesium for the dialysis fluid, and the introduction of the total magnesium results in a concentration of magnesium that is 0.04 to 0.10 mM per 1 mM citrate in the dialysis fluid greater than the prescribed concentration of total magnesium.

13. The method of claim 12 wherein the determination of the prescribed magnesium concentration determines the prescribed magnesium concentration to be one of 0.50 mM, 0.6 mM, and 0.75 mM.

* * * * *